US008512238B2

(12) United States Patent
Nissilä et al.

(10) Patent No.: US 8,512,238 B2
(45) Date of Patent: Aug. 20, 2013

(54) METHOD, PERFORMANCE MONITOR AND COMPUTER PROGRAM FOR DETERMINING PERFORMANCE

(75) Inventors: Juuso Nissilä, Ii (FI); Arto Niva, Jääli (FI); Jukka Jaatinen, Kempele (FI); Hannu Kinnunen, Oulu (FI)

(73) Assignee: Polar Electro Oy, Kempele (FI)

( * ) Notice: Subject to any disclaimer, the term of this patent is extended or adjusted under 35 U.S.C. 154(b) by 1086 days.

(21) Appl. No.: 11/545,018

(22) Filed: Oct. 6, 2006

(65) Prior Publication Data

US 2007/0082789 A1    Apr. 12, 2007

(30) Foreign Application Priority Data

Oct. 7, 2005    (FI) ..................................... 20055544

(51) Int. Cl.
*A63B 24/00*    (2006.01)

(52) U.S. Cl.
USPC ........... 600/300; 600/301; 128/903; 128/904; 128/905; 128/920; 482/4; 482/8

(58) Field of Classification Search
USPC .................. 600/300, 301; 128/903–905, 920
See application file for complete search history.

(56) References Cited

U.S. PATENT DOCUMENTS

| | | | |
|---|---|---|---|
| 4,408,613 A | 10/1983 | Relyea | |
| 5,081,991 A | 1/1992 | Chance | |
| 5,158,093 A * | 10/1992 | Shvartz et al. | 600/483 |
| 5,769,755 A * | 6/1998 | Henry et al. | 482/8 |
| 5,921,891 A * | 7/1999 | Browne | 482/8 |
| 5,976,083 A | 11/1999 | Richardson et al. | |
| 6,176,241 B1 * | 1/2001 | Blau et al. | 128/898 |
| 2004/0102931 A1 * | 5/2004 | Ellis et al. | 702/188 |
| 2004/0171460 A1 * | 9/2004 | Park | 482/8 |
| 2005/0228237 A1 * | 10/2005 | Shallenberger | 600/300 |
| 2007/0219059 A1 * | 9/2007 | Schwartz et al. | 482/8 |

FOREIGN PATENT DOCUMENTS

| | | |
|---|---|---|
| CA | 2355849 A1 | 7/2000 |
| EP | 0688533 A1 | 12/1995 |
| EP | 0709058 A1 | 5/1996 |
| EP | 0829226 A1 | 3/1998 |
| WO | WO 81/01507 | 6/1981 |
| WO | WO00/40151 | 7/2000 |
| WO | WO 02/07814 | 1/2002 |

OTHER PUBLICATIONS

"The significance of the aerobic-anaerobic transition for the determination of work load intensities during endurance training" European Journal of Applied Physiology and Occupational Physiology Sep. 1979, vol. 42, Issue 1, pp. 25-34.*

* cited by examiner

*Primary Examiner* — Bill Thomson
*Assistant Examiner* — Shirley Jian
(74) *Attorney, Agent, or Firm* — Hoffmann & Baron, LLP (57) ABSTRACT

The invention relates to a method, a user-specific performance monitor and a computer program for determining the user's performance. In the method, the performance power of a physical exercise is determined by means of user movement data registered by the user-specific performance monitor. Further, the exertion level corresponding to the performance power of the physical exercise is determined by means of physiological information measured from the user, the physiological information being registered by the user-specific performance monitor; and the user's performance is estimated by means of the performance power of the physical exercise and the exertion level corresponding to the performance power of the physical exercise.

20 Claims, 6 Drawing Sheets

METHOD, PERFORMANCE MONITOR AND COMPUTER PROGRAM FOR DETERMINING PERFORMANCE

CROSS-REFERENCE TO RELATED APPLICATION

This application claims priority to Finnish Patent Application Serial No. 20055544, filed on Oct. 7, 2005, which is incorporated herein by reference.

BACKGROUND OF THE INVENTION

1. Field of the Invention

The invention relates to a method for determining the performance of the user of a user-specific performance monitor on the basis of a physical exercise by the user; to a user-specific performance monitor; and to a computer program for determining the performance of the user of a user-specific performance monitor.

2. Description of the Related Art

One object of a physical exercise is to affect the performer's performance, which characterizes the adaptation of the performer's system and possibly the adaptation of the performance technique to the physical exercise.

The development of miniature measuring electronics has enabled the use of portable user-specific performance monitors for monitoring physical exercises. Thus, performance can be determined with a user-specific performance monitor.

In prior art solutions for user-specific performance monitors, the determination of the user's performance is based on the use of rest pulse rate parameters and personal physiological parameters, such as the user's age and weight. Determination of the performance enabled by rest pulse rate parameters and personal physiological parameters is, however, limited to determination that is carried out when the user is at rest. Hence, consideration of other techniques for determining the user's performance is needed.

SUMMARY OF THE INVENTION

An object of the invention is to implement a method, a user-specific performance monitor and a computer program in such a way that the performance of the user of the performance monitor can be determined reliably and, from the user's point of view, easily.

As a first aspect of the invention, a method is provided for determining the performance of the user of a user-specific performance monitor on the basis of a physical exercise by the user, the method comprising: determining the performance power of the physical exercise by means of user movement data registered by the user-specific performance monitor; determining the exertion level corresponding to the performance power of the physical exercise by means of physiological information measured from the user, the physiological information being registered by the user-specific performance monitor; and estimating the user's performance by means of the performance power of the physical exercise and the exertion level corresponding to the performance power of the physical exercise.

As a second aspect of the invention, a user-specific performance monitor is provided, comprising: performance power determination means for determining the performance power of a physical exercise by the user by means of user movement data; exertion level determination means for determining the exertion level corresponding to the user's physical exercise by means of physiological information measured from the user; and performance estimation means for estimating the user's performance by means of the performance power of the physical exercise and the exertion level corresponding to the performance power of the physical exercise.

As yet another aspect of the invention, a computer program is provided for determining the performance of the user of a user-specific performance monitor on the basis of a physical exercise by the user, which computer program comprises coded instructions for executing a computer process in a digital processor, the computer process comprising: determining the performance power of the physical exercise of the user by means of user movement data registered by the user-specific performance monitor; determining the exertion level corresponding to the performance power of the physical exercise by the user by means of physiological information measured from the user, the physiological information being registered by the user-specific performance monitor; and estimating the user's performance by means of the performance power of the physical exercise and the exertion level corresponding to the performance power of the physical exercise.

Preferred embodiments of the invention are described in independent claims.

The invention is based on determining, on the basis of user movement data, the performance power of a physical exercise, which characterizes the physical work by the user, shown outwards. The exertion level corresponding to the physiological exercise is determined on the basis of physiological information measured from the user, and it characterizes the work by the human system required for producing the performance power. The user's performance is estimated by means of the performance power and exertion level.

The invention provides several advantages. It allows the performance to be determined on the basis of movement data and physiological information collected during an exercise, and it does not require utilization of user information, the user's rest state, a stationary state or laboratory conditions, for example.

BRIEF DESCRIPTION OF THE DRAWINGS

The invention will now be described in greater detail in connection with preferred embodiments, referring to the attached drawings, in which.

DETAILED DESCRIPTION OF THE PREFERRED EMBODIMENTS

Figure 1:
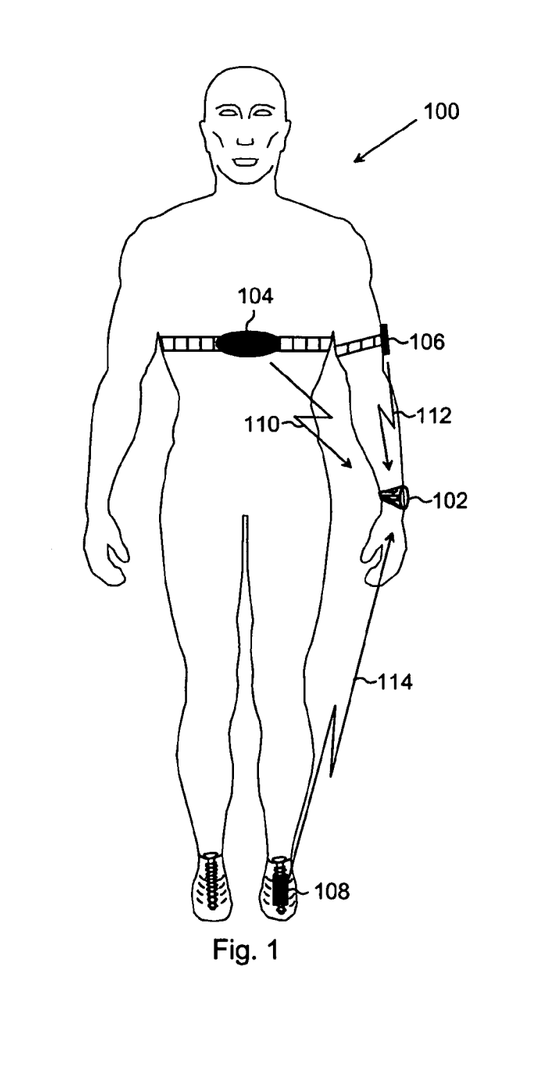
FIG. 1 shows a first example of an embodiment of the performance monitor.

Referring to FIG. 1, let us study an example of a user-specific performance monitor comprising a central processing unit 102, an ECG probe 104 and a movement determination unit 106, 108. The user-specific performance monitor is, in the example of FIG. 1, shown as a distributed system. In some embodiments, parts of the user-specific performance monitor shown in FIG. 1 may be positioned in the same unit, such as in the central processing unit 102 and/or the ECG probe. To illustrate its structure and functioning, the user-specific performance monitor is positioned on the user's 100 body.

The ECG probe 104 shows an example of a device measuring physiological information from the user. The physiological information characterizes the user's physiological state and may comprise the user's pulse rate frequency, user's pulse rate interval, variation of the user's pulse rate interval, user's temperature, user's blood pressure, amount of the user's perspiration and/or user's electromyogram variable. The provided solution is not, however, confined to the above-mentioned physical information but may be any physiological information measurable from the user of the performance monitor.

It is characteristic of the user-specific performance monitor that the user 100 himself/herself as the object of the performance measurement monitors on the user-specific performance monitor and gives the necessary use commands to the recorder. The exercise is typically a physical exercise, such as running, walking and/or cycling, without being limited to these examples. In this context, the user-specific performance monitor is briefly called 'performance monitor', the user of the performance monitor being called 'user 100'.

The ECG probe 104 determines the electrocardiogram for instance on the user's 100 skin surface during a physical exercise and transmits a pulse rate communication signal 110 received from the electrocardiogram to the central processing unit 102. The pulse rate communication signal 110 can be understood generally as a signal containing physiological information.

The pulse rate communication signal 110 may be a signal transmitted via wireless or wire transmission. The pulse rate communication signal 110 may comprise the user's pulse rate information that may comprise the timing burst characterizing individual pulse rate, the pulse rate frequency, pulse rate interval and/or pulse rate parameters generated from the pulse rate frequency and/or pulse rate interval, such as variance of the pulse rate interval. In one embodiment, the ECG probe 104 transmits timing bursts to the central processing unit 102 that determines the timing of the timing bursts and generates from the timing of the timing bursts pulse rate information, such as pulse rate frequency and/or pulse rate interval, and possibly secondary pulse rate parameters that can be determined mathematically, for instance, on the basis of the pulse rate frequency and/or pulse rate interval.

The movement determination unit 106, 108 measures movement relating to the physical activity by the user 100 and may transmit to the central processing unit 102 a movement communication signal 112, 114 transferring primary movement data. The movement communication signal 112, 114 may be a signal transmitted via wire or wireless transmission. Primary movement data may comprise acceleration measured from one of the user's 100 body parts, such as a limb, the user's 100 position or a movement parameter, such as pedal force and/or pedal power, measured from the transmission mechanism of pedal equipment. Thus, secondary movement information, such as the user's velocity, may be determined in the central processing unit 102. In one embodiment, the movement determination unit 106, 108 comprises means for generating secondary movement information, in which case the movement communication signal 112, 114 transmits secondary movement information.

In one embodiment, the movement determination unit 106, 108 is integrated into the central processing unit 102. In such a case, the movement communication signal 112, 114 is transmitted from the movement determination unit 106, 108 in the central processing unit 102 as an electric signal that may comprise a bit string.

In one embodiment, the movement determination unit 108 comprises one or more movement sensors, such as an acceleration sensor, which measures the acceleration of the user's limb, for example. Parameters of the user's 100 state of movement, such as velocity, can be deduced from the acceleration of the limb. Thus, the movement communication signal 114 may comprise acceleration values and/or a kinetic variable, such as velocity, generated from the acceleration value. The movement communication signal may be a signal transmitted via wire or wireless transmission.

In one embodiment, the movement determination unit 106 comprises a positioning device, such as a GPS (Global Positioning System) device, which determines the user's 100 location and possibly velocity by using an external reference for determining the location. In such a case, the movement communication signal 112 may comprise the user's location information, velocity, height and/or acceleration.

In one embodiment, the central processing unit 102 receives and registers the movement communication signal 112, 114 and the pulse rate communication signal 110, and processes movement information transmitted by the movement communication signal 112, 114 and pulse rate information transmitted by the pulse rate communication signal 110, for instance by means of computation algorithms. Computation algorithms allow determination of the performance power of a physical exercise and/or the exertion level corresponding to the performance power of the physical exercise. The user's performance can be further calculated from the performance power and exertion level. In addition, the central processing unit 102 may store pulse rate information, movement information, performance power values, exertion level values and/or performance values.

In one embodiment of the provided solution, the central processing unit 102 is a wrist device to be attached to the user's wrist. In another embodiment, the central processing unit is integrated into the pulse rate determination unit 104 that may be of a type of a chest band.

A physical exercise is a physical activity by the user in which physical performance power is released from the user's 100 body. A physical exercise may be a running exercise, walking exercise, skating exercise, gym exercise, cycling or any physical exercise in which measurable physical performance power is released from the user. Physical performance power may be released for example as movement of the body or a body part of the user, movement of a vehicle used by the user or power generated by fitness equipment. Physical performance power may be characterized for instance by means of the user's proceeding velocity, mechanical power generated by the user and/or the user's oxygen consumption value, i.e. VO2 value.

Physical performance power is determined by means of the user's 100 movement information, such as velocity, acceleration and/or movement parameter measured from the pedal of pedal equipment. Physical performance power $P_i$ can be presented in the mathematical form $$P_i = f(MP, C), \quad (1)$$

in which the index i refers to measurement i, variable MP is a movement parameter and C is a performance coefficient. The movement parameter MP is for example a function of velocity, and the performance coefficient C is a conversion coefficient that standardizes different types of exercises, such as running, walking and cycling, on the same scale. For instance, in the case of a running exercise, function (1) is expressed as $$VO2 = 3.2 \times v, \quad (2)$$

in which the performance power $P_i$ of expression (1) is presented by means of the oxygen consumption value VO2, the movement parameter MP is presented by means of velocity v, and the performance coefficient C=3.2 is a scaling factor typical of a running exercise.

In a physical exercise, the user's 100 system tends to compensate for a change in the metabolism, such as in the energy and oxygen requirement, caused by the physical exercise, which expresses itself as the exertion level experienced by the user. The physical exertion corresponding to physical performance power can be determined by means of physiological information measured from the user. The correspondence of the exertion level to the physical performance power refers, in this context, to how high an exertion level the given physical performance power causes to the user.

The exertion level can be characterized by a variable received from physiological information, such as the user's pulse rate frequency, pulse rate interval and/or variation of the pulse rate interval.

The user's 100 performance typically characterizes the adaptation of his/her system and possibly the adaptation of the performance technique to the physical exercise. Performance typically indicates the exertion level directed at the user's system at a given performance power value. When the performance is low, given performance power causes a high exertion level, whereas when the performance is high, the same performance power causes a lower exertion level.

In an embodiment, the performance is estimated by calculating the relation between the constant pulse rate frequency and performance power at a maximum pulse rate frequency. Thus, estimating the performance can be expressed as $$F = A \times \left(\frac{HR_{max}}{HR}\right) \times P_{out} + D \quad (3)$$

where HR is the measured pulse rate frequency, $HR_{max}$ is the maximum pulse rate frequency, $P_{out}$ is the performance power of the physical exercise, A is the scaling factor, such as 1, and D is a parameter typical of the exercise. For instance for a running exercise, D=3.5. The pulse rate reserve can be calculated from the user information fed to the performance monitor, and/or it may be deduced from pulse rate values registered in previous activities.

In one embodiment, the performance is estimated by utilizing the user's maximum pulse rate and/or rest pulse rate. In such a case, calculating the performance can be expressed as $$F = \frac{HR_{max} - HR_r}{HR - HR_r} \times P_{out} + D \quad (4)$$

where $HR_{max}$ is the maximum pulse rate frequency and $HR_r$ is the rest pulse rate.

The rest and the maximum pulse rate may have been programmed in the performance monitor in advance, and/or they can be deduced from pulse values registered in previous activities.

Theoretical performance power at a fixed exertion level may be used as a performance indicator. A fixed exertion level may be determined for instance at a fixed pulse rate frequency. An example of this is expression (4), in which the fixed pulse rate frequency is the maximum pulse rate, and the performance indicator is the performance power at a maximum pulse rate. If the oxygen consumption value, for example, is used as the performance indicator, expression (4) gives the maximum oxygen consumption value, i.e. oxygen uptake. In this case, the development of the performance can be monitored by means of the maximum oxygen consumption value.

As an advantage of the provided solution, performance can be determined performance-power-specifically at a submaximum exertion level, and determining the performance does not require use of several exertion levels successively. Determination of performance according to the provided solution allows monitoring of not only the user's physiological performance but also the effect of the performance technique of a physical exercise on the exertion level. Hence, the performance technique relating to the exercise is also a factor affecting the performance.

It is to be noted that when using expressions (3) and/or (4), persons skilled in the art do not confine themselves to using the pulse rate frequency or derivatives of the pulse rate frequency but may position the pulse rate interval or a derivative of the pulse rate interval in the expressions. Furthermore, corresponding expressions may be written for other types of physiological information.

Figure 2:
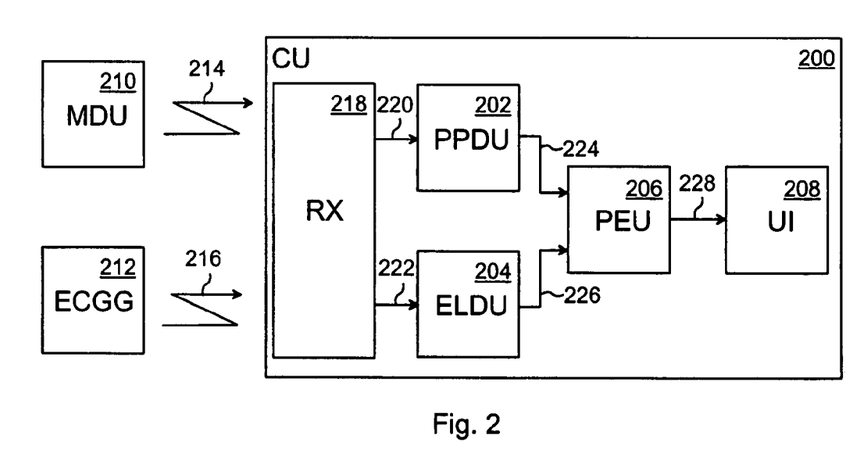
FIG. 2 shows a second example of an embodiment of the performance monitor.

With reference to FIG. 2, let us study an embodiment of the performance monitor in which the performance monitor comprises a central processing unit (CU) 200, a movement determination unit (MDU) 210 and an ECG probe (ECGG) 212. In this case, the ECG probe 212 is an example of a device measuring physiological information.

The movement determination unit 210 communicates a movement communication signal 214 to the central processing unit 200.

The ECG probe 212 communicates a pulse rate communication signal 216 to the central processing unit 200.

The central processing unit 200 comprises a receiver unit (RX) 218 that receives a movement communication signal 214 and a pulse rate communication signal 216. In one embodiment, separate receiver units are used in receiving the movement communication signal 214 and the pulse rate communication signal 216.

The movement communication signal 214 may be an electromagnetic signal, such as a radio frequency signal of 2.4 GHz.

The pulse rate communication signal 216 may be an electromagnetic signal of 5 kHZ or a radio frequency signal of 2.4 GHz. The provided solution is not, however, limited to these frequencies.

The receiver unit 218 typically comprises a receiver antenna and receiver electronics that, for example, converts a high-frequency signal to baseband and performs analogue-to-digital conversions and signal filtering. The structure of receivers in performance monitors is known per ser to a person skilled in the art.

The receiver unit 218 converts the movement communication signal 214 into a movement data bit string 220 and inputs the movement data bit string 220 to a performance power determination unit (PPDU) 202. The movement data bit string 220 comprises the user's movement data, such as the value of the velocity and/or pedal parameter.

In an embodiment, the performance power determination unit 202 determines the physical performance power from the movement bit string 220. If the movement data is velocity data and the exercise is running, the performance power can be determined for instance by means of expression (1). In an embodiment, the performance power is determined in the movement determination unit 210 if there is sufficiently processing power in the movement determination unit 210. In such a case, the movement communication signal 214 and the movement data bit string 220 may contain the performance power value as such, the movement determination unit 210 being part of the performance power determination means.

The receiver unit 218 converts the pulse rate communication signal 216 into a pulse rate data bit string 222 and inputs the pulse rate data bit string 222 to the exertion level determination unit (ELDU) 204. The pulse rate data bit string 222 comprises the user's pulse rate information, such as values of the timing of successive bursts and/or pulse rate variable values.

The performance power determination unit 202 inputs a performance power signal 224 containing the performance power data to a performance estimation unit (PEU) 206.

The exertion level determination unit 204 determines the exertion level corresponding to the performance power and inputs an exertion level signal 226 containing exertion level data to the performance estimation unit 206.

The performance estimation unit 206 estimates the performance power of the performance of the user and the exertion level corresponding to the performance power of a physical exercise by using expressions (3) to (4).

The performance estimation unit 206 may transmit the value 228 of a performance-characterizing variable to a user interface 208 that presents the value 228 of the performance-characterizing variable to the user 100 graphically and/or numerically.

The performance determination unit 202 of the central processing unit 200, the exertion level determination unit 204 and the performance determination unit 206 may be implemented by means of a computer program executed in a digital processor of the central processing unit 200, for example.

Figure 3:
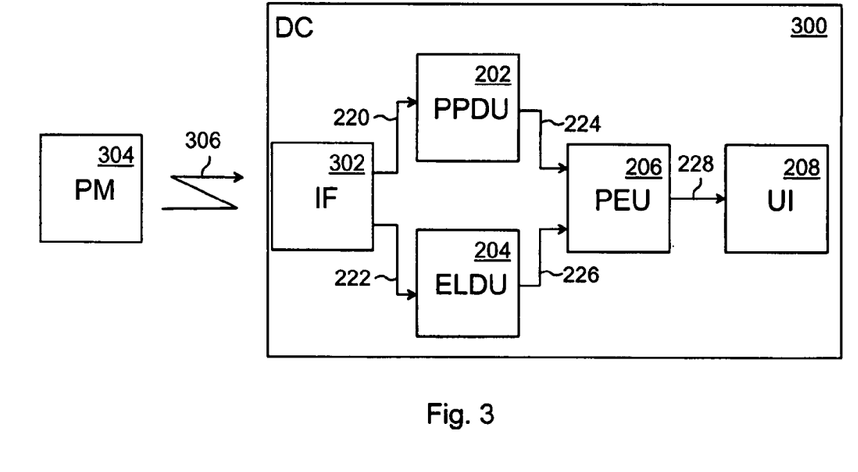
FIG. 3 shows an example of an embodiment of the provided solution.

With reference to FIG. 3, let us study a data processing device (DC) 300 comprising a performance power determination unit 202, an exertion level determination unit 204 and a performance determination unit 206.

The performance power determination unit 202 and the exertion level determination unit 204 are connected to an interface means 302 that receives a communication signal 306 from a performance monitor 304. The interface means 302 is a wireless receiver or a wired bus connecting the data processing device and the performance monitor. The communication signal 306 comprises movement data and pulse rate data generated by the performance monitor 306.

The performance power determination unit 202 of the data processing device 300, the exertion level determination unit 204 and the performance determination unit 206 may be implemented for instance by means of a computer program executed in a digital processor of the central processing unit 200.

According to the example of FIG. 2, the user's 100 movement data and pulse rate data are registered by means of the performance monitor, and the performance can be monitored and analyzed during an exercise and/or after an exercise.

With the data processing device according to the example of FIG. 3, the user's 100 movement data and pulse rate data are registered by means of the performance monitor during an exercise. The movement data and pulse rate data are transmitted from the performance monitor to the data processing device, and the user's 100 performance can be analyzed after the exercise.

Figure 4:
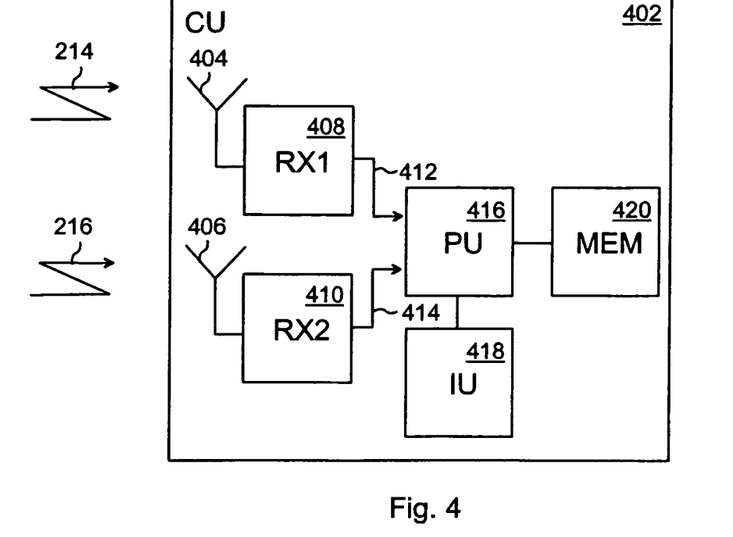
FIG. 4 shows an example of the central processing unit of the performance monitor.

With reference to FIG. 4, let us study an example of a central processing unit 402 of the performance monitor. The central processing unit 402 of the example comprises a first receiver 408 for receiving a movement communication signal 214, and a second receiver 410 for receiving a pulse rate communication signal 216.

The first receiver 408 is a receiver of 5 kHz or 2.4 GHz, for example.

The second receiver 410 is a receiver of 5 kHz or 2.4 GHz, for example.

The first receiver 408 is connected to a first antenna unit 404.

The second receiver 410 is connected to a second antenna unit 406.

In an embodiment, the first receiver 408 and the second receiver 410 form one integrated receiver.

The first receiver 408 receives a movement communication signal 214, converts the movement communication signal 214 into a baseband movement data bit string 412 and inputs the movement data bit string 412 to a processing unit 416.

The second receiver 410 receives a pulse rate communication signal 216, converts the pulse rate communication signal 216 into a baseband pulse rate data bit string 414 and inputs the pulse rate data bit string 414 to the processing unit 416.

The processing unit performs tasks of the performance power determination unit 202, exertion level determination unit 204 and performance determination unit 206 by means of a computer program stored in a memory unit 420.

The processing unit 416 may be connected to a user interface 418 that displays the value 228 of the performance-characterizing variable to the user 100 graphically and/or numerically. Further, the user interface 418 may comprise input means, such a keypad, with which the user 100 is able to input user data and/or commands to the performance monitor.

Figure 5:
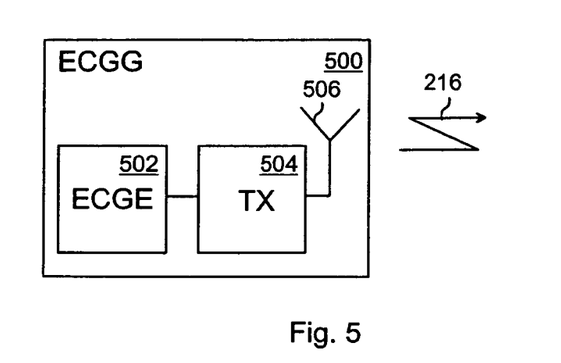
FIG. 5 shows an example of an ECG probe.

With reference to FIG. 5, let us consider an example of an ECG probe 500. The ECG according to the example comprises ECG electrodes (ECGE) 502 that measure electric impulses induced by the ECG from the user's skin surface. The ECG electrodes 502 are connected to a transmitter unit (TX) 504 that generates a pulse rate communication signal 216 from electric impulses and transmits a pulse rate communication signal 216 via an antenna 506.

In an embodiment, the ECG probe comprises means, such as AND converters, filters and a digital processor, for processing digital signals of a digital processor. In this case, the ECG probe may generate a pulse rate communication signal coded digitally and determine higher-level pulse rate data, such as values of pulse rate parameters.

Figure 6:
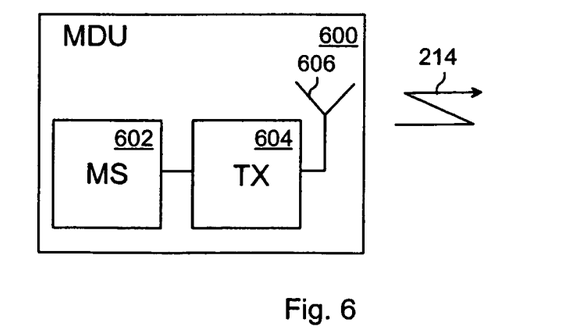
FIG. 6 shows an example of a movement determination unit.

With reference to FIG. 6, let us examine an example of a movement determination unit 600.

The movement determination unit 600 comprises a movement sensor 602 that determines primary movement data, such as acceleration and/or the user's position. The movement sensor 602 may further comprise processing means, such as a digital processor, determining secondary movement data, such as the user's 100 velocity, on the basis of the primary movement data. The movement sensor may be an acceleration sensor or a GPS receiver.

The movement determination unit 600 may further comprise a transmitter 604 connected to the movement sensor 602, which transmitter generates a movement communication signal 214 and transmits a movement communication signal 214 via an antenna 606.

Figure 7:
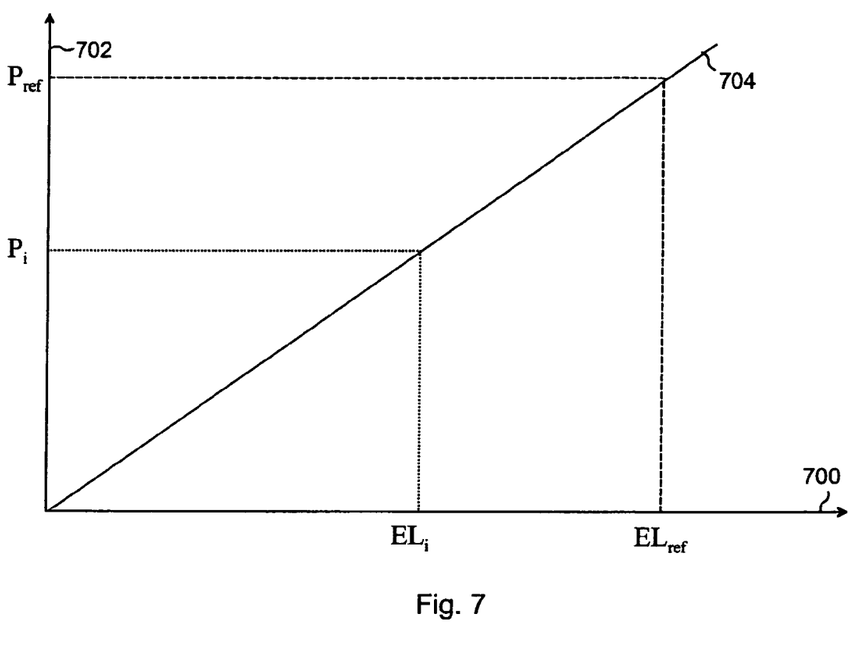
FIG. 7 shows a graphical example of the relation between a pulse rate variable and the performance power of a physical exercise.

With reference to FIG. 7 let us examine, with the aid of a graphical representation, an example of determining performance. The x axis 700 of FIG. 7 indicates exertion level (EL), such as the pulse rate frequency value in a unit of pulse rate variable, whereas the y axis 702 indicates performance power (P) for instance in a unit of proceeding velocity or oxygen consumption value.

In an embodiment, the performance power determination unit 202 determines at least one momentary performance power value $P_i$, and the exertion level determination unit 204 determines the exertion level value $EL_i$ corresponding to the momentary performance power value $P_i$. Performance can be estimated by using relation 704 between performance power and exertion level known as such, such as linear or piecewise linear relation, for instance by calculating performance power value ($L_{ref}$) corresponding to a reference value ($EL_{ref}$) of the exertion level. The reference value of the exertion level may be, for example, a maximum pulse rate, in which case the corresponding performance power is the maximum performance.

Figure 8:
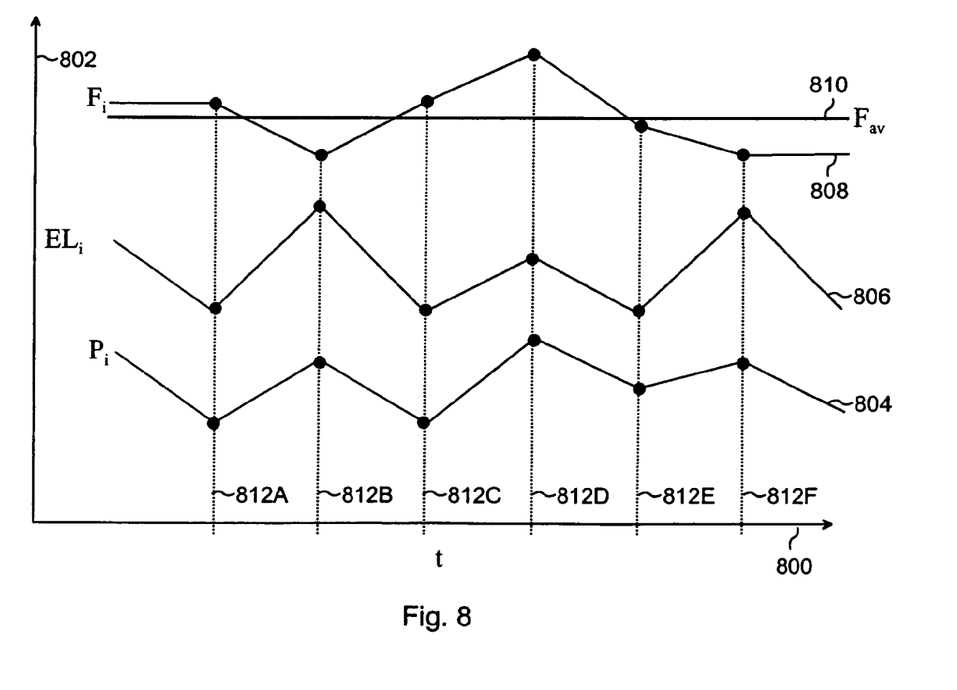
FIG. 8 shows a graphical example of performance determination.

With reference to FIG. 8, let us examine a graphical example of performance determination by utilizing measurement data. The x axis 800 of the example denotes time in a unit of time, such as seconds, while the y axis 802 indicates a performance power curve 804, an exertion level curve 806 corresponding to the performance power curve, and a performance curve 808.

The measurement data is comprised of the performance power value and the exertion level value determined at measurement times 812A, 812B, 812C, 812D, 812E, 812F. The performance power values $P_i$ are presented as black dots at a performance power curve 804. The performance power values $EL_i$ are presented as black dots at an exertion level curve 806.

On the basis of each determined performance power value $P_i$ and the exertion level value $EL_i$, a performance value $F_i$ is determined by utilizing the expression (3) to (6) and/or the graphical representation of FIG. 7, for example. This gives performance data indicated as black dots at a performance curve 808.

On the basis of the performance data, a performance average value $F_{av}$ 810 can be determined, indicated on the horizontal line. In determining the performance average value, statistically deviating performance data may be ignored.

The performance power values, exertion level values and possibly performance values determined at different times may be stored in a memory unit 420 of the performance monitor, from which they may be read for determining the performance average value.

Figure 9:
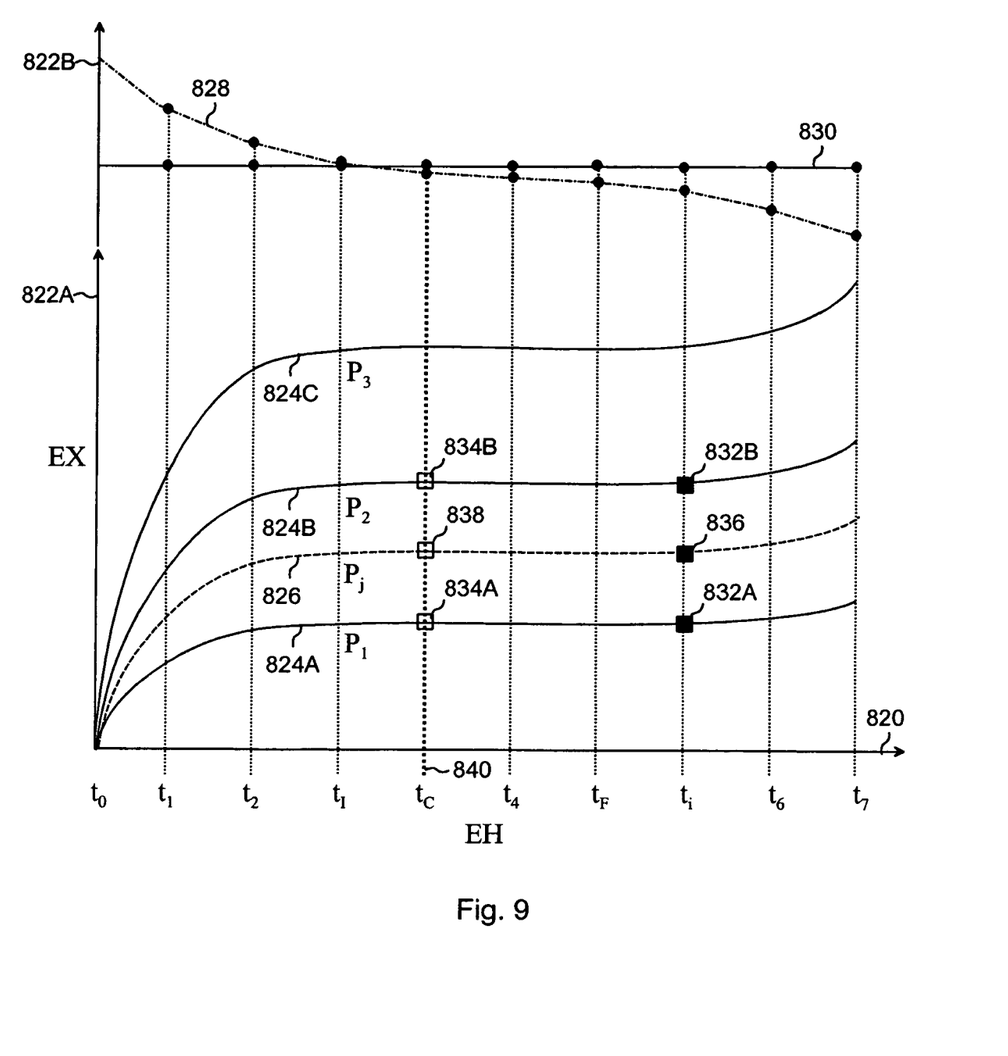
FIG. 9 shows a graphical example of pulse rate frequency and performance as a function of the exertion history.

FIG. 9 shows a set of exertion curves 842A, 842B, 842C, which indicates for instance the pulse rate HR or the value of a pulse rate variable comparable to the pulse rate as a function of the exertion history (EH). Each exertion curve 842A, 824B, 824C indicates the value of exertion at a constant performance power. Thus, performance power $P_1$ corresponds to the exertion curve 824A, performance power $P_2$ corresponds to the exertion curve 824B, and performance power $P_3$ corresponds to the exertion curve 824C. In the example shown, $P_1 < P_2 < P_3$.

The horizontal axis 820 shows the exertion history in minutes, for example. The exertion history can also be shown as pulse rate accumulation or another variable characterizing time history.

The vertical axis 822A shows exertion for instance in a unit of pulse rate, such as bpm (beats per minute) or as percents of the pulse rate reserve. Further, the vertical axis 822B shows an uncorrected performance curve 828 and a corrected performance curve 830.

It is characteristic of the exertion curve 824A to 824C that at the beginning of the exertion history, such as during the interval of times $t_0$ and $t_1$, the exertion value corresponding to the constant performance power is lower than the real value. Thus, between the times $t_0$ and $t_1$, the uncorrected performance curve 828 gives a performance value more optimistic than the real value.

When the exertion history has higher values, such as after time $t_F$, the exertion curve 824A to 824C grows for instance as a result of tiredness, even if the performance power remains constant. Hence, after the times $T_F$ the performance curve 828 gives a performance value more pessimistic than the real value.

In one embodiment, the performance estimation unit 206 takes into account the effect of the exertion history on the physiological information, such as pulse rate, measured from the user. The effect of the exertion history can be taken into account by selecting the performance power data characterizing the performance power of the physical exercise and the exertion data characterizing the exertion level corresponding to the performance power of the physical exercise, used in estimating performance, on the basis of the exertion history. Thus, for example, in estimating the performance it is possible to confine oneself to utilizing the performance power and physiological information measured between times $t_C$ and $t_F$. In one embodiment, $t_C = 3$ min and $t_F = 60$ min.

In one embodiment, the performance estimation means 206 take into account the effect of the exertion history on the physiological information measured from the user by transforming the exertion data characterizing the exertion level corresponding to the performance power of a physical exercise to a constant exertion history point. The constant exertion history point can be denoted with $t_c$ at the time axis, and it can be selected freely. In one embodiment, the exertion history point is selected at the point of 12 minutes.

Let us assume that points 832A and 834A of the exertion curve 824A and points 832B and 834B of the exertion curve 824B are previously known and stored for instance in the memory unit 420 of the central processing unit 402. Let us further assume that no exertion curve 826 corresponding to the measured performance power $P_j$ is available and that the measurement time $t_i$ is not at the point of the constant exertion point $t_c$. Thus, the exertion level corresponding to the measurement time $t_i$ can be transformed to the constant exertion history point $t_C$, for instance with the expression $$HR_{C,j} = HR_{C,1} + \frac{HR_{i,j} - HR_{i,1}}{HR_{i,2} - HR_{i,1}} \times (HR_{C,2} - HR_{C,1}) \quad (5)$$

where $HR_{C,j}$ is the value 838 of the exertion curve 826 corresponding to the measured performance power $P_j$ in the constant exertion history point $t_C$; $HR_{i,j}$ is exertion 836 determined for the measurement time $t_i$; $HR_{i,1}$ is the value 832A of the exertion curve 824A corresponding to the performance power $P_1$ at the measurement time $t_i$; $HR_{i,2}$ is the value 832B of the exertion curve 824B corresponding to the performance power $P_2$ at the measurement time $t_i$; $HR_{C,1}$ is the value of the exertion curve 824A corresponding to the performance power $P_1$ at the constant exertion history point $t_C$; and $HR_{C,2}$ is the value 834B of the exertion curve 824B corresponding to the performance power $P_2$ in the constant exertion history point $t_C$.

The provided solution allows the exertion history to be taken into consideration at any point of the exertion history. If the performance values measured at a different point $t_i$ of the exertion history are presented at the horizontal axis 820, a corrected performance curve 830 is produced.

Figure 10:
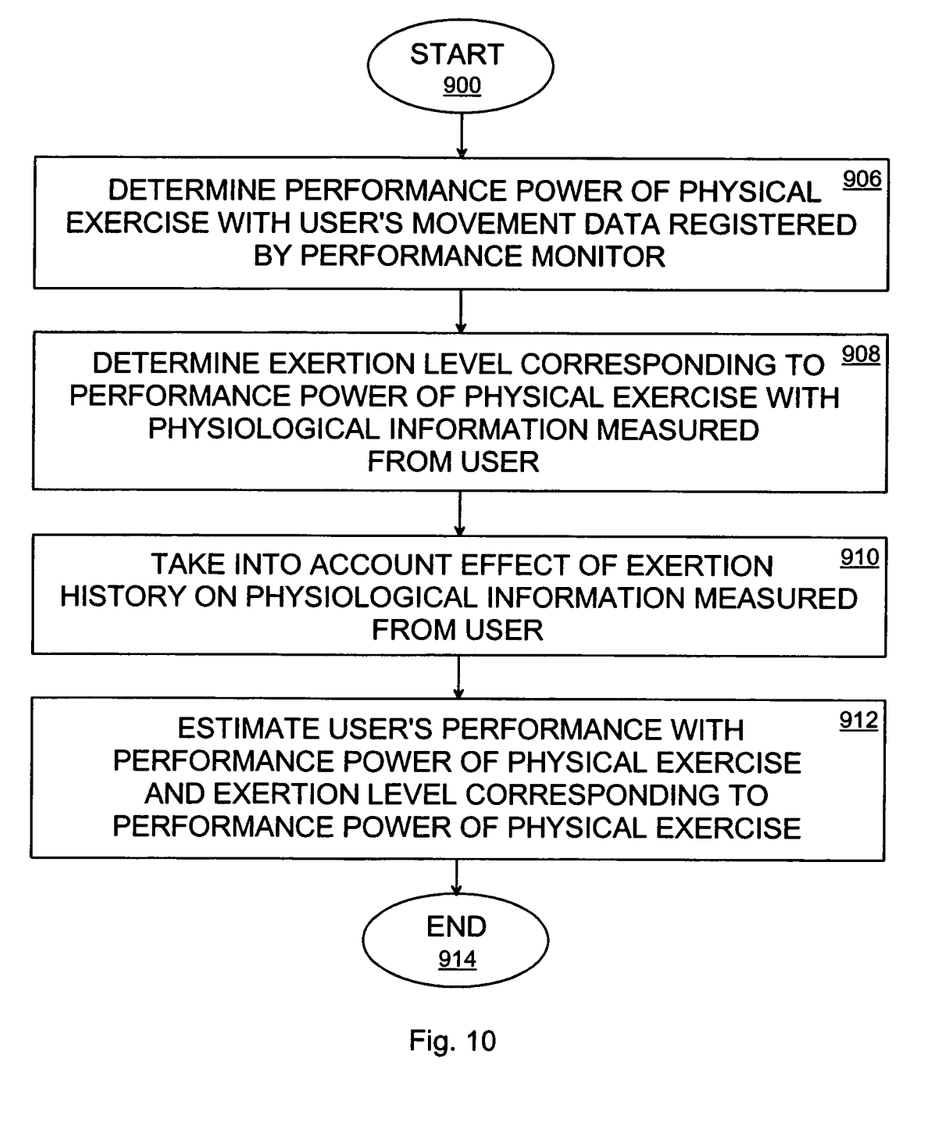
FIG. 10 shows a first example of the method according to an embodiment.

In FIG. 10, an example is presented of embodiments of the method of the provided solution.

The method starts at 900.

At 906, the performance power of a physical exercise is determined by means of the user's movement data, which has been registered by a user-specific performance monitor.

At 908, the exertion level corresponding to the performance power of the physical exercise is determined by means of physiological information measured from the user, the physiological information having been registered by the user-specific performance monitor.

At 910, the effect of the exertion history on the physiological information measured from the user is taken into account.

In one embodiment, the effect of the exertion history on the physiological information measured from the user is taken into account 910 by selecting the performance power data characterizing the performance power of the physical exercise and the exertion data characterizing the exertion level corresponding to the performance power of the physical exercise, used in estimating performance, on the basis of the exertion history.

In one embodiment, the effect of the exertion history on the physiological information measured from the user is taken into account 910 by transforming the exertion data characterizing the exertion level corresponding to the performance power of the physical exercise to a constant exertion history point.

At 912, the user's performance is estimated with the performance power of the physical exercise and the exertion level corresponding to the performance power of the physical exercise.

At 914, the method ends.

Figure 11:
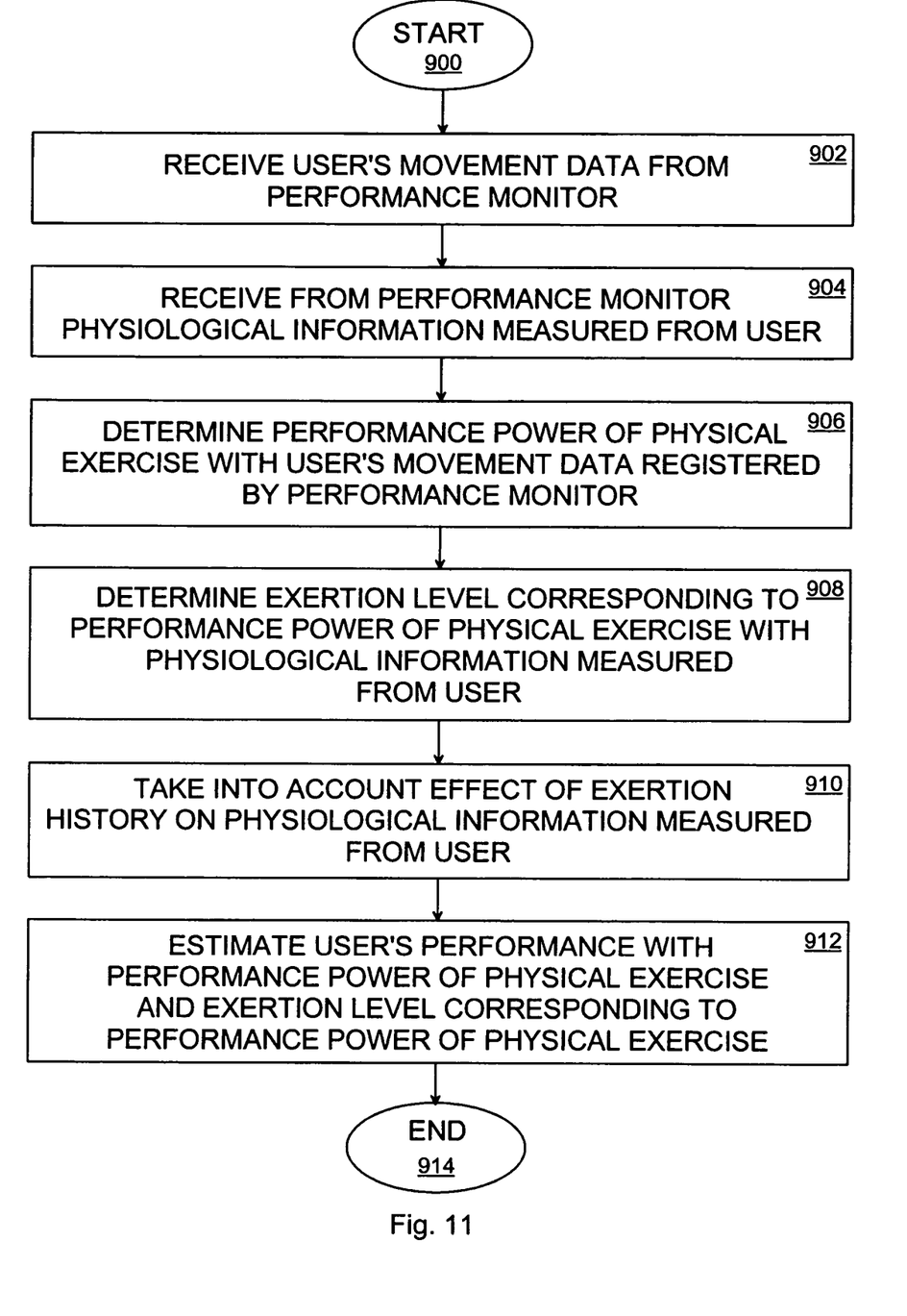
FIG. 11 shows a second example of the method according to an embodiment.

FIG. 11 shows examples of a computer process according to the provided solution, at least some of which can be executed in a digital processing unit 416 of a performance monitor and/or in a processor of a data processing device.

The process starts at 900.

At 902, the user's movement data is received from a user-specific performance monitor.

At 904, physiological information measured from the user is received from the user-specific performance monitor.

At 906, the performance power of a physical exercise is determined by means of the user's movement data, which has been registered by the user-specific performance monitor.

At 908, the exertion level corresponding to the performance power of the physical exercise is determined with the physiological information measured from the user, the physiological information having been registered by the user-specific performance monitor.

At 910, the effect of the exertion history on the physiological information measured from the user is taken into account.

In one embodiment, the effect of the exertion history on the physiological information measured from the user is taken into account 910 by selecting the performance power data characterizing the performance power of the physical exercise and the exertion data characterizing the exertion level corresponding to the performance power of the physical exercise, used in estimating the performance, on the basis of the exertion history.

In one embodiment, the effect of the exertion history on the physiological information measured from the user is taken into account 910 by transforming the exertion data characterizing the exertion level corresponding to the performance power of the physical exercise to a constant exertion history point.

At 912, the user's performance is estimated by means of the performance power of the physical exercise and the exertion level corresponding to the performance power of the physical exercise.

At 914, the process ends.

The computer program may be executed in the processing unit 420 of the central processing unit 402 of the performance monitor and stored in the memory unit 420 of the central processing unit of the performance monitor. In some embodiments, parts of the computer program are executed in a digital processor of the ECG probe 500 and/or digital processor of the movement determination unit 600.

In one embodiment, the computer program is executed in a digital processor of the data processing device 300.

The computer program may be stored in a computer program distribution medium. The medium may be any known means for distributing the computer program from the manufacturer/vendor to the end user.

The distribution medium may be, for example, a medium readable by a data processing means, a program-storing medium or a storing medium, a memory readable by a data processing device or a software distribution package, and a signal understood by a data processing means, a telecommunication signal or a compressed software package.

In one embodiment, the computer program is included in a computer software product and/or computer program distribution medium.

Although the invention has been described above with reference to the example of the attached drawings, it is obvious that it is not restricted to it but can be modified in a plurality of ways within the scope of the attached claims.

The invention claimed is:

1. A data processing device comprising:
a digital processor configured to receive a user's movement data relating to the user's physical activity during a physical exercise, the digital processor being configured to receive the user's pulse rate data, the digital processor being configured to determine the performance power of a physical exercise by the user by means of the movement data, wherein the performance power represents a function of the movement data, the digital processor being configured to determine the exertion level corresponding to the user's physical exercise by means of the user's pulse rate data, wherein the exertion level represents physiological information associated with the user, the digital processor being configured to estimate the user's performance by means of the performance power and the exertion level corresponding to the performance power by transforming exertion data representing the exertion level corresponding to the performance power to a specified exertion history point, wherein the performance characterizes the user's adaptation to the physical exercise.

2. The data processing device according to claim 1 wherein the digital processor is further configured to use a theoretical performance power at a fixed exertion level as a performance indicator.

3. The data processing device according to claim 2, wherein the digital processor is further configured to use maximum oxygen uptake as a performance indicator.

4. The data processing device according to claim 1, wherein the digital processor is further configured to transmit a performance-characterizing variable to a user interface for presenting the performance-characterizing value to the user graphically or numerically.

5. A data processing device comprising:
a digital processor configured to receive a user's movement data relating to the user's physical activity during a physical exercise, the digital processor being configured to receive the user's pulse rate data, the digital processor being configured to determine the performance power of a physical exercise by the user by means of the movement data, wherein the performance power represents a function of the movement data, the digital processor being configured to determine the exertion level corresponding to the user's physical exercise by means of the user's pulse rate data, wherein the exertion level represents physiological information associated with the user, the digital processor being configured to estimate the user's performance by means of the performance power and the exertion level by calculating the relation between a constant pulse rate frequency and performance power at a maximum pulse rate frequency,
the digital processor being configured to transmit a performance-characterizing variable to a user interface for presenting the performance-characterizing value to the user graphically or numerically.

6. The data processing device according to claim 5, wherein the digital processor is further configured to use a theoretical performance power at a fixed exertion level as a performance indicator.

7. The data processing device according to claim 6, wherein the digital processor is further configured to use maximum oxygen uptake as a performance indicator.

8. The data processing device according to claim 5, wherein the digital processor is further configured to transmit a performance-characterizing variable to a user interface for presenting the performance-characterizing value to the user graphically or numerically.

9. A data processing device comprising:
a digital processor configure to receive a user's movement data relating to the user's physical activity during a physical exercise, the digital processor being configured to receive the user's pulse rate data, the digital processor being configured to determine the performance power of a physical exercise by the user by means of the movement data, wherein the performance power represents a function of the movement data, the digital processor being configured to determine the exertion level corresponding to the user's physical exercise by means of the user's pulse rate data, wherein the exertion level represents physiological information associated with the user, the digital processor being configured to estimate the user's performance by means of the performance power and the exertion level by utilizing an equation, $$F = \frac{HR_{max} - HR_r}{HR - HR_r} \times P_{out} + D,$$

wherein HR is a measured pulse rate frequency, $HR_{max}$ is a maximum pulse rate frequency, $P_{out}$ is a performance power of the physical exercise, $HR_r$ is a rest pulse rate frequency, F is the user's performance, and D is a parameter typical of the exercise, the digital processor being configured to transmit a performance-characterizing variable to a user interface for presenting the performance-characterizing value to the user graphically or numerically.

10. The data processing device according to claim 9, wherein the digital processor is further configured to use a theoretical performance power at a fixed exertion level as a performance indicator.

11. The data processing device according to claim 10, wherein the digital processor is further configured to use maximum oxygen uptake as a performance indicator.

12. The data processing device according to claim 9, wherein the digital processor is further configured to transmit a performance-characterizing variable to a user interface for presenting the performance-characterizing value to the user graphically or numerically.

13. A method of processing data comprising:
receiving, by a processing device, a user's movement data relating to the user's physical activity during a physical exercise;
receiving, by the processing device, the user's pulse rate data;
determining, by the processing device, the performance power of a physical exercise by the user by means of the movement data, wherein the performance power represents a function of the movement data;
determining, by the processing device, the exertion level corresponding to the user's physical exercise by means of the user's pulse rate data, wherein the exertion level represents physiological information associated with the user;
estimating, by the processing device, the user's performance by means of the performance power and the exertion level by calculating the relation between a constant pulse rate frequency and performance power at a maximum pulse rate frequency; and
transmitting, by the processing device, a performance-characterizing variable to a user interface for presenting the performance-characterizing value to the user graphically or numerically.

14. The method of data processing according to claim 13, further comprising using, by the processing device, a theoretical performance power at a fixed exertion level as a performance indicator.

15. The method of data processing according to claim 14, further comprising using, by the processing device, maximum oxygen uptake as a performance indicator.

16. The method of data processing according to claim 13, further comprising transmitting, by the processing device, a performance-characterizing variable to a user interface for presenting the performance-characterizing value to the user graphically or numerically.

17. A method of processing data comprising:
receiving, by a processing device, a user's movement data relating to the user's physical activity during a physical exercise;
receiving, by the processing device, the user's pulse rate data;
determining, by the processing device, the performance power of a physical exercise by the user by means of the movement data, wherein the performance power represents a function of the movement data;
determining, by the processing device, the exertion level corresponding to the user's physical exercise by means of the user's pulse rate data, wherein the exertion level represents physiological information associated with the user;

estimating, by the processing device, the user's performance by means of the performance power and the exertion level by utilizing an equation, $$F = \frac{HR_{max} - HR_r}{HR - HR_r} \times P_{out} + D,$$

wherein HR is a measured pulse rate frequency, $HR_{max}$ is a maximum pulse rate frequency, $P_{out}$ is a performance power of the physical exercise, $HR_r$ is a rest pulse rate frequency, F is the user's performance, and D is a parameter typical of the exercise; and transmitting, by the processing device, a performance-characterizing variable to a user interface for presenting the performance-characterizing value to the user graphically or numerically.

18. The method of data processing according to claim 17, further comprising using, by the processing device, a theoretical performance power at a fixed exertion level as a performance indicator.

19. The method of data processing according to claim 18, further comprising using, by the processing device, maximum oxygen uptake as a performance indicator.

20. The method of data processing according to claim 17, further comprising transmitting, by the processing device, a performance-characterizing variable to a user interface for presenting the performance-characterizing value to the user graphically or numerically.

* * * * *